(12) United States Patent
Allen, IV et al.

(10) Patent No.: US 8,961,513 B2
(45) Date of Patent: Feb. 24, 2015

(54) SURGICAL TISSUE SEALER

(75) Inventors: James D. Allen, IV, Broomfield, CO (US); Gary M. Couture, Longmont, CO (US); James S. Cunningham, Boulder, CO (US); David M. Garrison, Longmont, CO (US); Sean T. O'Neill, Campbell, CA (US); Jason T. Sanders, Johnstown, CO (US); Robert M. Sharp, Boulder, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 503 days.

(21) Appl. No.: 13/358,136

(22) Filed: Jan. 25, 2012

(65) Prior Publication Data

US 2013/0190760 A1 Jul. 25, 2013

(51) Int. Cl.
*A61B 18/18* (2006.01)

(52) U.S. Cl.
USPC .......................................................... 606/51

(58) Field of Classification Search
USPC .......................................................... 606/51
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| 4,503,855 A | 3/1985 | Maslanka |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,300,082 A | 4/1994 | Sharpe et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,443,479 A | 8/1995 | Bressi, Jr. |
| D384,413 S | 9/1997 | Zlock et al. |
| 5,693,051 A | 12/1997 | Schulze et al. |
| 5,752,973 A | 5/1998 | Kieturakis |
| H1745 H | 8/1998 | Paraschac |
| D402,028 S | 12/1998 | Grimm et al. |
| 5,876,401 A | 3/1999 | Schulze et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — George Manuel

(57) ABSTRACT

A surgical instrument is provided. The surgical instrument includes an end effector assembly including first and second jaw members moveable relative to one another between a first, spaced-apart position and a second position proximate tissue, wherein, in the second position, the jaw members cooperate to define a cavity that is configured to receive tissue between the jaw members and a resilient electrically conductive sealing surface operably coupled to at least one jaw member, the resilient electrically conductive sealing surface selectively positionable from a first unflexed position to a second flexed position.

18 Claims, 5 Drawing Sheets

(56) References Cited

U.S. PATENT DOCUMENTS

| | | | |
|---|---|---|---|
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,123,701 A | 9/2000 | Nezhat | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,485,489 B2 | 11/2002 | Teirstein et al. | |
| D493,888 S | 8/2004 | Reschke | |
| 6,786,905 B2 | 9/2004 | Swanson et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,169,145 B2 | 1/2007 | Isaacson et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,438,714 B2 | 10/2008 | Phan | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,949,407 B2 | 5/2011 | Kaplan et al. | |
| 7,955,326 B2 | 6/2011 | Paul et al. | |
| D649,249 S | 11/2011 | Guerra | |
| D649,643 S | 11/2011 | Allen, IV et al. | |
| 2003/0069570 A1 | 4/2003 | Witzel et al. | |
| 2003/0078577 A1* | 4/2003 | Truckai et al. | 606/51 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026 179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.

(56) References Cited

OTHER PUBLICATIONS

U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.

(56) References Cited

OTHER PUBLICATIONS

Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL TISSUE SEALER

BACKGROUND

The present disclosure relates to surgical instruments and, more particularly, to a surgical tissue sealing for grasping, sealing and/or dividing tissue.

TECHNICAL FIELD

A forceps is a pliers-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

SUMMARY

In accordance with one embodiment of the present disclosure, a surgical instrument is provided. The surgical instrument includes an end effector assembly including first and second jaw members moveable relative to one another between a first, spaced-apart position and a second position proximate tissue, wherein, in the second position, the jaw members cooperate to define a cavity that is configured to receive tissue between the jaw members and a resilient electrically conductive sealing surface operably coupled to at least one jaw member, the resilient electrically conductive sealing surface selectively positionable from a first unflexed position to a second flexed position.

The present disclosure also provides an end effector assembly including first and second jaw members moveable relative to one another between a first, spaced-apart position and a second position proximate tissue, wherein, in the second position, the jaw members cooperate to define a cavity that is configured to receive tissue between the jaw members, wherein at least one of the jaw members includes a resilient electrically conductive sealing surface that is selectively flexible toward tissue grasped between the jaw members to apply a pressure to the tissue from about 3 kg/cm$^2$ to about 16 kg/cm$^2$.

A method for sealing tissue is also contemplated by the present disclosure. The method includes grasping tissue between first and second jaw members moveable relative to one another between a spaced-apart position and a second position proximate tissue, wherein, in the approximated position, the jaw members cooperate to define a cavity that is configured to receive tissue grasped between the jaw members; and flexing toward the grasped tissue a resilient electrically conductive sealing surface disposed within at least one of the jaw members.

BRIEF DESCRIPTION OF THE DRAWINGS

Various embodiments of the present disclosure are described herein with reference to the drawings wherein.

DETAILED DESCRIPTION

Figure 1:
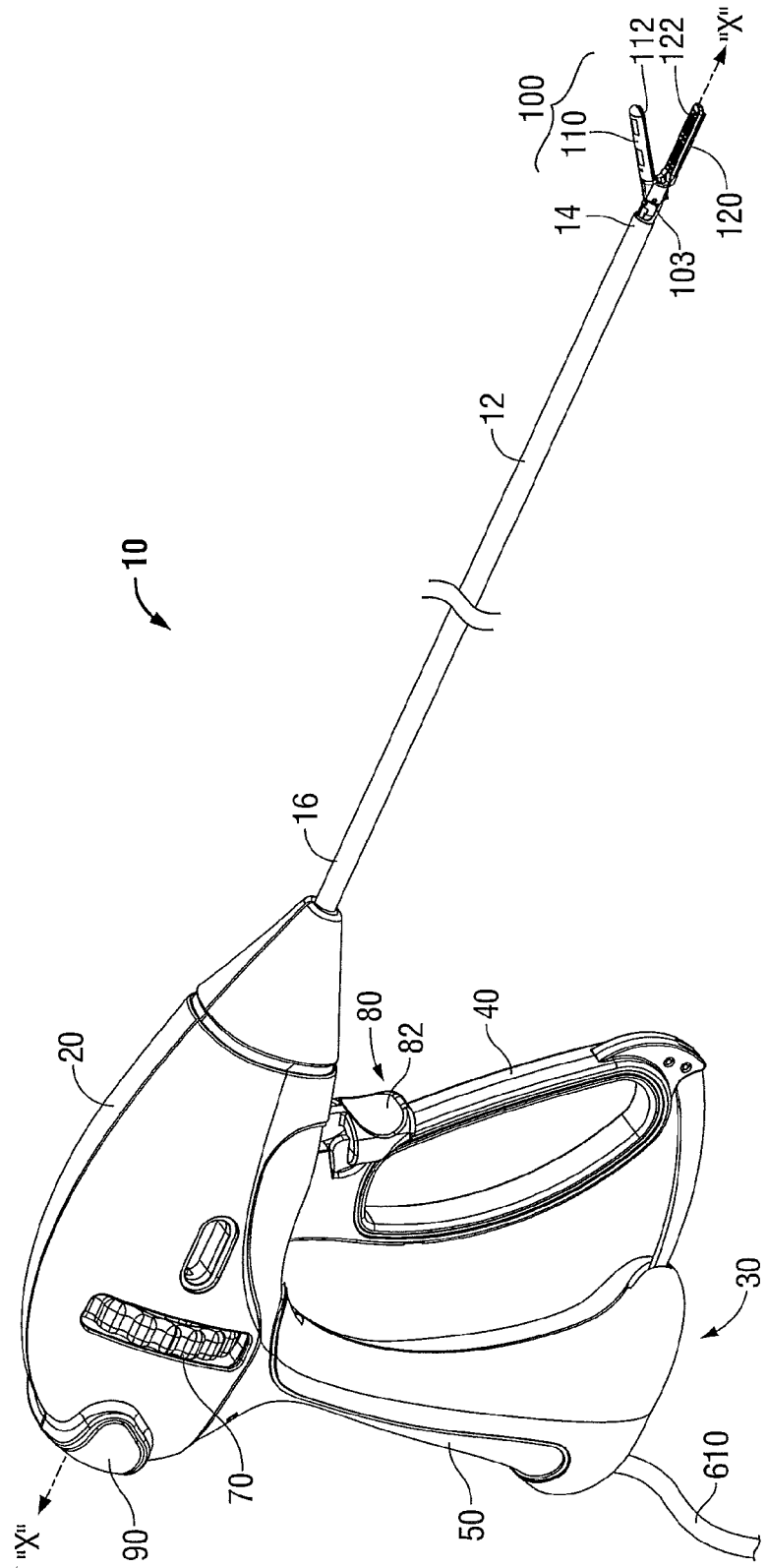
FIG. 1 is a front, perspective view of an endoscopic surgical instrument configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
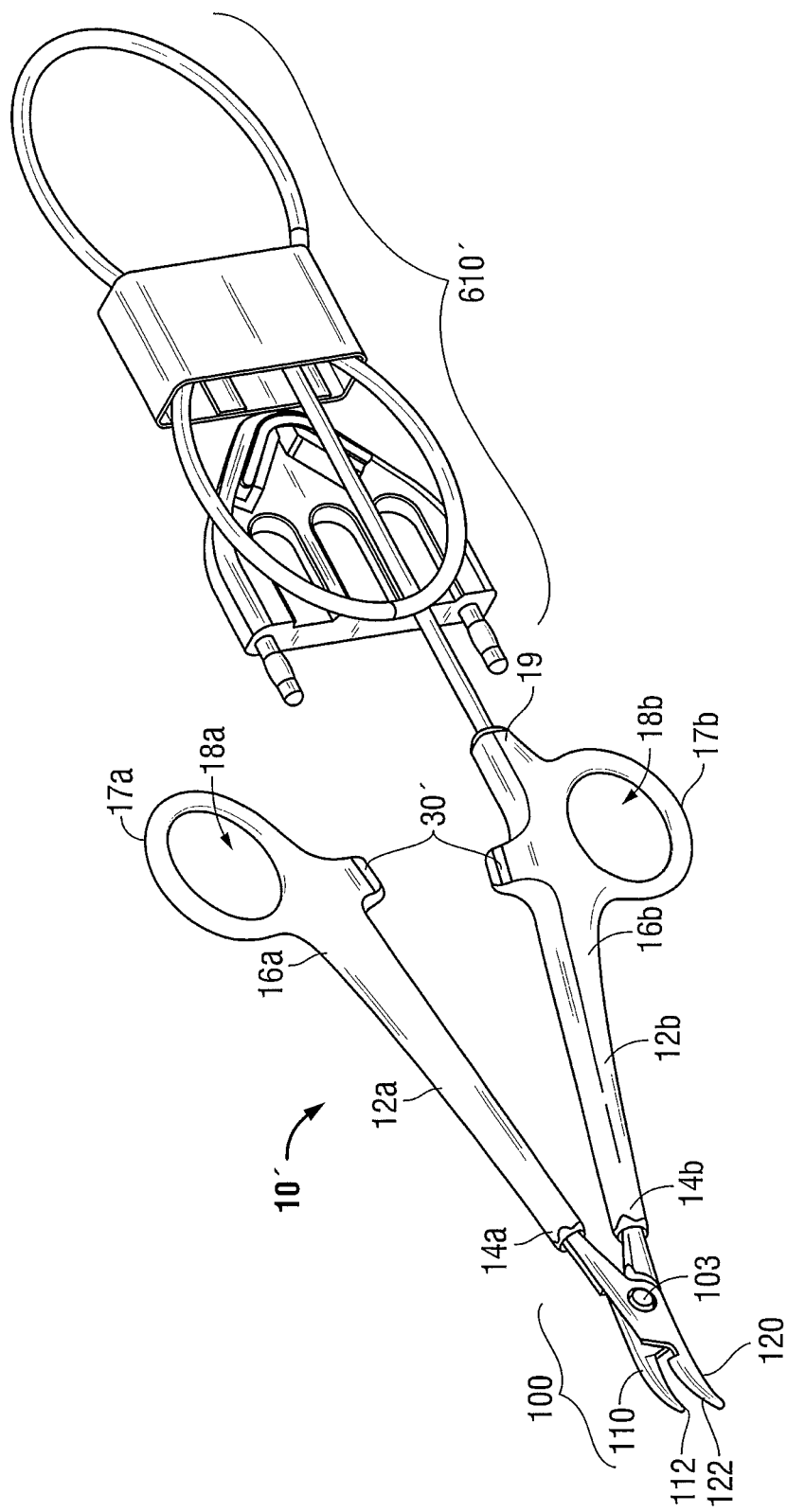
FIG. 2 is a front, perspective view of an open surgical instrument configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not explicitly shown) or other suitable power source, although forceps 10 may alternatively be configured as a battery powered instrument. Cable 610 includes a wire (or wires) (not explicitly shown) extending therethrough that has sufficient length to extend through shaft 12 in order to provide electrical energy to at least one of the jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of jaw members 110 and 120 includes an electrically conductive tissue sealing surface 112, 122, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. In some embodiments, a knife assembly (not explicitly shown) is disposed within shaft 12 and a knife channel (not explicitly shown) is defined within one or both jaw members 110, 120 to permit reciprocation of a knife blade (not explicitly shown) therethrough, e.g., via activation of trigger 82 of trigger assembly 80. The particular features of end effector assembly 100 will be described in greater detail hereinbelow.

Continuing with reference to FIG. 1, moveable handle 40 of handle assembly 30 is ultimately connected to a drive assembly (not explicitly shown) that, together, mechanically cooperate to impart movement of jaw members 110 and 120 between a spaced-apart position and an approximated position to grasp tissue disposed between sealing surfaces 112 and 122 of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. The ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 which is designed to connect the forceps 10' to a source of energy such as an electrosurgical generator (not explicitly shown). Proximal shaft connector 19 secures an electrosurgical cable 610' to forceps 10' such that the user may selectively apply electrosurgical energy to the electrically conductive sealing surfaces 112 and 122 (FIG. 1) of jaw members 110 and 120, respectively, as needed.

Forceps 10' may further include a knife assembly (not explicitly shown) disposed within either of shafts 12a, 12b and a knife channel (not explicitly shown) defined within one or both jaw members 110, 120 to permit reciprocation of a knife blade (not explicitly shown) therethrough.

Figure 3A:
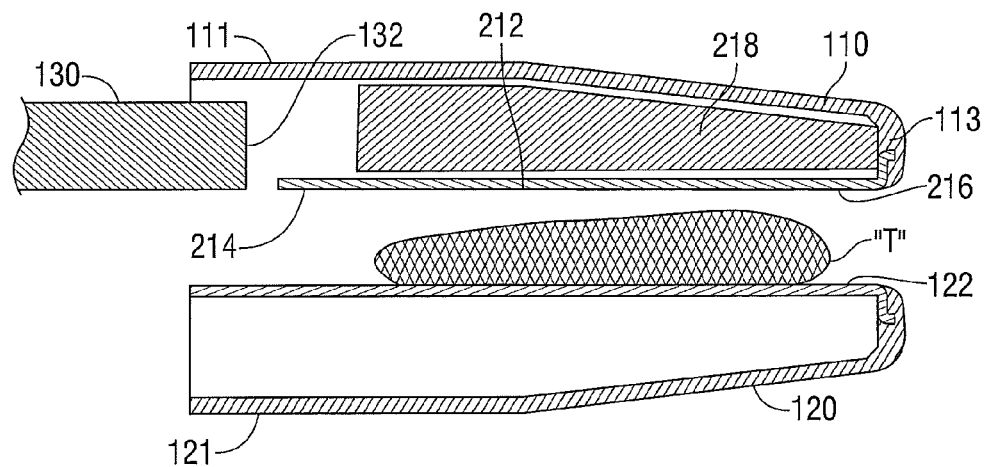
FIG. 3A is an enlarged, side, cross-sectional view of one embodiment of an end effector assembly configured for use with the surgical instrument of FIG. 1 or 2 wherein jaw members of the end effector assembly are positioned about tissue.
Figure 3B:
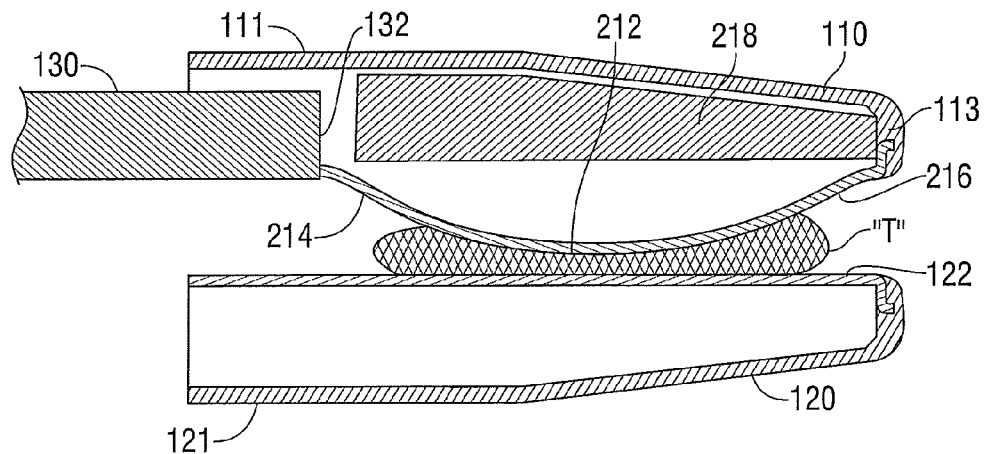
FIG. 3B is an enlarged, side, perspective view of the end effector assembly of FIG. 3A wherein the jaw members are shown approximating tissue under a specified tissue pressure.

Turning now to FIGS. 3A and 3B, jaw members 110 and 120 include jaw housings 111 and 121, respectively. The end effector assembly 100, including jaw members 110 and 120 is configured for use with either instrument 10 or instrument 10', discussed above, or any other suitable surgical instrument. However, for purposes of simplicity and consistency, end effector assembly 100 will be described hereinbelow with reference to instrument 10 only.

As shown in FIGS. 3A-3B, the jaw member 110 includes a resilient electrically conductive sealing surface 212. In some embodiments, both of the jaw members 110 and 120 may include a resilient conductive sealing surface. The sealing surface 212 may be formed as a conductive plate electrode having a freely movable proximal end 214 and a distal end 216. The sealing surface 212 is coupled to a distal end 113 of the jaw housing 111 at its distal end 216. The sealing surface 212 is supported within the jaw housing 111 of the jaw member 110 by a support member 218, which is not coupled thereto and prevents the sealing surface 212 from flexing inwardly.

The sealing surface 212 may be formed from any suitable reversibly resilient conductive material including, but not limited to, medical grade metals and plating materials, such as stainless steel, titanium, aluminum, nickel, alloys and combinations thereof. In some embodiments, the sealing surface 212 may be formed from a non-conductive material that includes a layer of a resilient, electrically conductive material formed from the metals described above. Suitable non-conductive materials include, but not limited to, plastic, carbon fiber, and combinations thereof. The non-conductive material also includes a layer of an elastic, electrically conductive material formed from the metals described above. The term "reversibly resilient" as used herein denotes that the material retains its shape after application of force below the elasticity limit (e.g., amount of pressure that irreversibly deforms the material) that is sufficient to bend the material. The term "medical grade" as used herein denotes a material that is chemically unreactive when brought in physical contact with tissue.

During operation, the jaw members 110 and 120 are brought into the approximated position to proximate tissue T disposed between sealing surfaces 212 and 122 of jaw members 110, 120, respectively. Thereafter, the sealing surface 212 is brought into further contact with the tissue T to apply pressure thereto. More particularly, forceps 10 (or 10') includes an actuation member 130 that is longitudinally movable (e.g., by actuating the movable handle 40 and/or the trigger 80) within the jaw member 110. The actuation member 130 includes an abutment surface 132 disposed at a distal end thereof that comes in contact with the proximal end 214 of the sealing surface 212, thereby causing the sealing surface 212 to flex downward toward the tissue T. As described above, the sealing surface 212 is prevented from flexing upwardly (e.g., into the jaw housing 111) by the support member 218. The longitudinal travel distance of the actuation member 130 in the distal direction may be limited to achieve a desired compression of the sealing surface 212.

The longitudinal travel distance of the actuation member 130 in the distal direction is proportional to the pressure applied by the sealing surface 212. In particular, the pressure applied may be adjusted as a function of the travel distance of the actuation member 130 and the elasticity of the sealing plate 212. In one embodiment, the sealing surface 212 is configured to apply a predetermined amount of pressure to the tissue T from about 3 kilograms per centimeter ($kg/cm^2$) to about 16 $kg/cm^2$. In other embodiments, from about 7 $kg/cm^2$ to about 12 $kg/cm^2$. This may be controlled by adjusting one or more of the following parameters including, but not limited to, dimensions of the sealing surface 212, material (e.g., tensile) properties of the sealing surface 212, and/or the travel distance of the actuation member 130. The sealing surface 212 may include a width of from about 0.25 millimeters (mm) to about 25 mm, a length of from about 1 mm to about 100 mm, and a thickness of from about 0.002 mm to about 2.5 mm. The sealing surface 212 may have an elasticity expressed as a tensile or Young's modulus from about 69 GPa (gigapascals) to about 300 GPa.

In some embodiments, the sealing surface 212 may be configured to snap into engagements with the tissue T when pressure is applied to the proximal end 214. In this instance, the sealing surface 212 is configured to apply a specific pressure against the tissue T from about 3 $kg/cm^2$ to about 16 $kg/cm^2$. In other embodiments from about 7 $kg/cm^2$ to about 12 $kg/cm^2$.

Figure 4A:
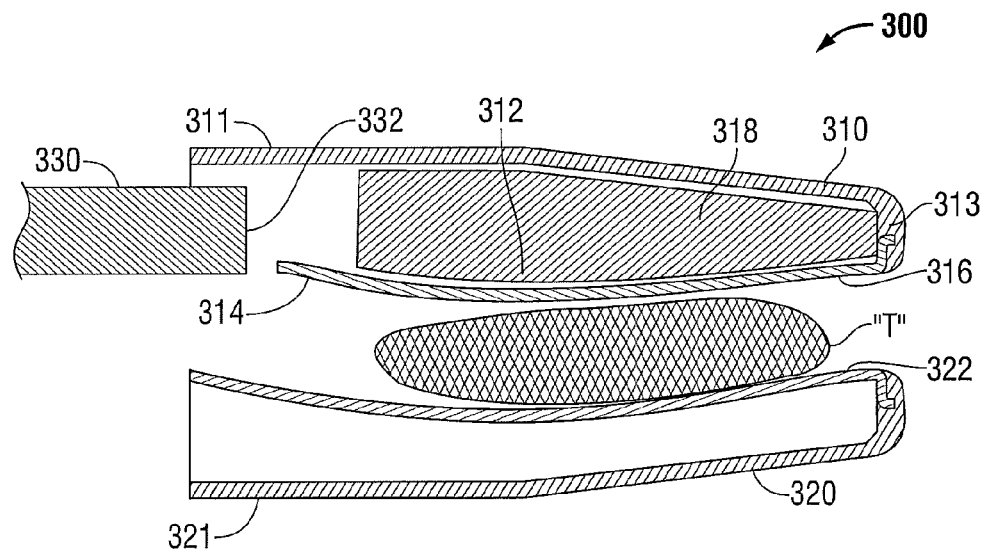
FIG. 4A is an enlarged, side, cross-sectional view of one embodiment of an end effector assembly configured for use with the surgical instrument of FIG. 1 or 2 wherein jaw members of the end effector assembly are positioned about tissue.
Figure 4B:
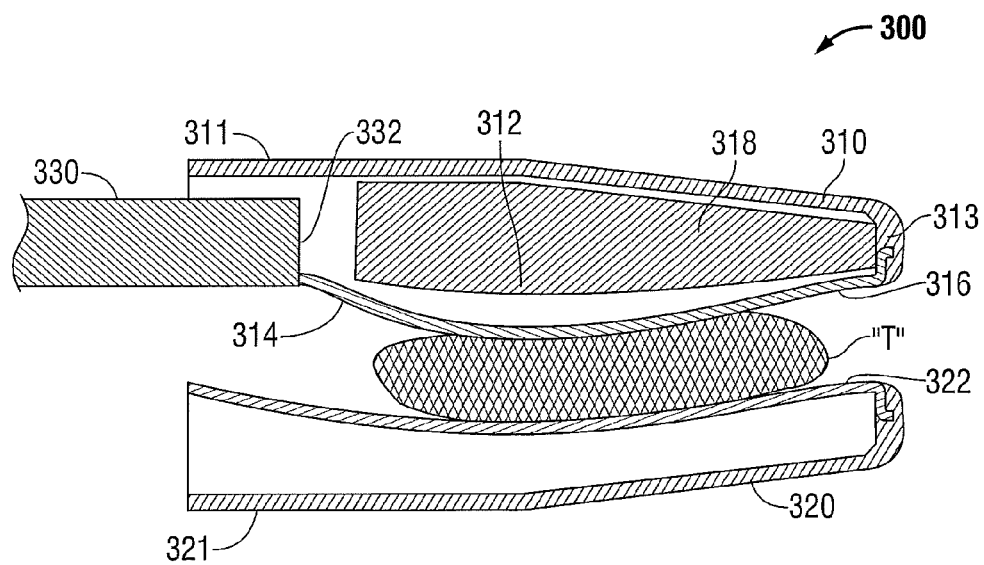
FIG. 4B is an enlarged, side, perspective view of the end effector assembly of FIG. 4A wherein the jaw members are shown approximating tissue under a specified tissue pressure.

With reference to FIGS. 4A and 4B, another embodiment of the end effector assembly 300 is shown. The end effector 300 is substantially similar to the end effector 100 and is configured for use with either instrument 10 or instrument 10', discussed above, or any other suitable surgical instrument. However, for purposes of simplicity and consistency, end effector assembly 300 will be described hereinbelow with reference to instrument 10 only.

The end effector 300 includes jaw members 310 and 320 having jaw housings 311 and 321, respectively. The jaw member 310 includes a resilient electrically conductive sealing surface 312. In some embodiments, both of the jaw members 310 and 320 may include a resilient conductive sealing surface. The sealing surface 312 may be formed as a conductive plate electrode having a freely movable proximal end 314 and a distal end 316. The sealing surface 312 is coupled to a distal end 313 of the jaw housing 311 at its distal end 316. The sealing surface 312 is supported within the jaw housing 311 of the jaw member 310 by a support member 318, which is not coupled thereto and prevents the sealing surface 312 from flexing inwardly. The sealing surfaces 312 and 322 may be formed from the same reversibly resilient materials as the sealing surfaces 212 and 122 of FIGS. 3A and 3B.

During operation, the jaw members 310 and 320 are brought into the approximated position to proximate tissue T disposed between sealing surfaces 312 and 322 of jaw members 310, 320, respectively. Thereafter, the sealing surface 312 is brought into further contact with the tissue T to apply pressure thereto via the actuation member 330 that is longitudinally movable (e.g., by actuating the movable handle 40 and/or the trigger 80) within the jaw member 310. The actuation member 330 includes an abutment surface 332 disposed at a distal end thereof that comes in contact with the proximal end 314 of the sealing surface 312, thereby causing the sealing surface 312 to flex downward toward the tissue T. As described above, the sealing surface 312 is prevented from flexing upwardly (e.g., into the jaw housing 311) by the support member 318. The longitudinal travel distance of the actuation member 330 in the distal direction may be limited to achieve a desired compression of the sealing surface 312.

The sealing surfaces 312 and 322 are precurved to allow for smaller actuation forces for flexing the sealing surface 312 downward. In particular, since the sealing surface 312 is precurved, the sealing surface 312 is more inclined to flex toward the tissue upon engagement by the actuation member 330. The sealing surface 312 is concave with respect to the tissue T, whereas the sealing surface 322 is convex, thus, maintaining a substantially uniform gap distance between the sealing surfaces 312 and 322. Curvature of the sealing surface 322 may be of substantially similar shape as the sealing surface 312 to allow for the tissue "T" to be evenly spread as the jaw members 310 and 320 are approximated thereabout.

The longitudinal travel distance of the actuation member 330 in the distal direction is proportional to the pressure applied by the sealing surface 312. In particular, the pressure applied may be adjusted as a function of the travel distance of the actuation member 330 and the elasticity of the sealing plate 312. In one embodiment, the sealing surface 312 is configured to apply a predetermined amount of pressure to the tissue T from about 3 kilograms per centimeter ($kg/cm^2$) to about 16 $kg/cm^2$. In other embodiments, from about 7 $kg/cm^2$ to about 12 $kg/cm^2$. This may be controlled by adjusting one or more of the following parameters including, but not limited to, dimensions of the sealing surface 312, material (e.g., tensile) properties of the sealing surface 312, and/or the travel distance of the actuation member 330. The sealing surface 312 may include a width of from about 0.25 millimeters (mm) to about 25 mm, a length of from about 1 mm to about 100 mm, and a thickness of from about 0.002 mm to about 2.5 mm. The sealing surface 312 may have an elasticity expressed as a tensile or Young's modulus from about 69 GPa (gigapascals) to about 300 GPa.

Figure 5A:
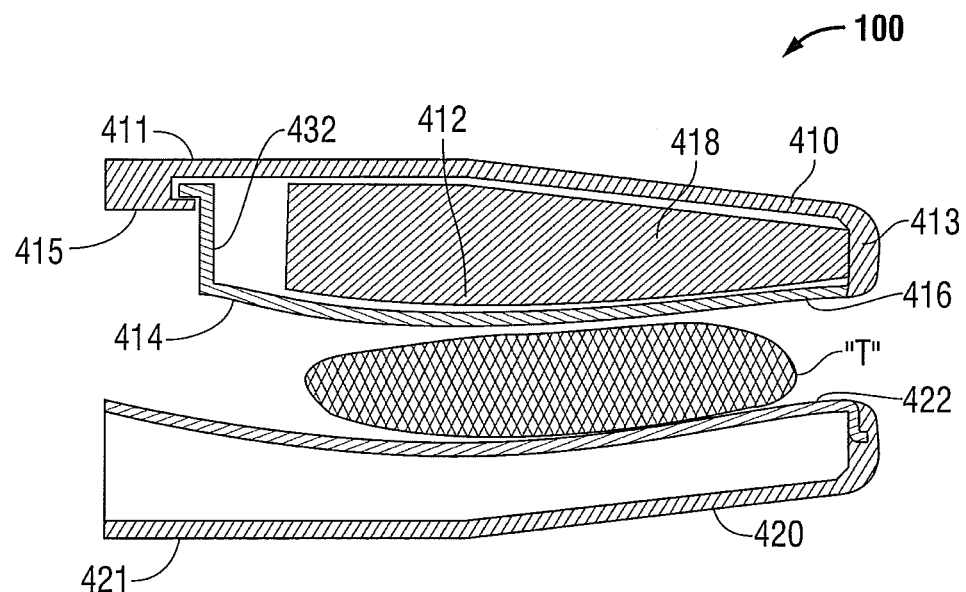
FIG. 5A is an enlarged, side, cross-sectional view of one embodiment of an end effector assembly configured for use with the surgical instrument of FIG. 1 or 2 wherein jaw members of the end effector assembly are positioned about tissue.
Figure 5B:
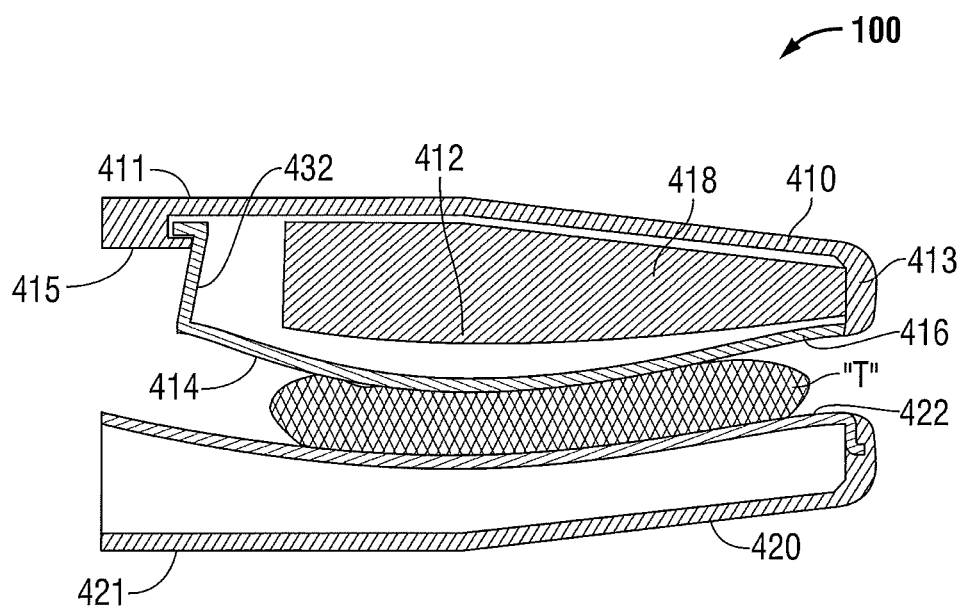
FIG. 5B is an enlarged, side, perspective view of the end effector assembly of FIG. 5A wherein the jaw members are shown approximating tissue under a specified tissue pressure.

With reference to FIGS. 5A and 5B, another embodiment of the end effector assembly 400 is shown. The end effector 400 is substantially similar to the end effector 100 and is configured for use with either instrument 10 or instrument 10', discussed above, or any other suitable surgical instrument. However, for purposes of simplicity and consistency, end effector assembly 400 will be described hereinbelow with reference to instrument 10 only.

The end effector 400 includes jaw members 410 and 420 having jaw housings 411 and 421, respectively. The jaw member 410 includes a resilient electrically conductive sealing surface 412. In some embodiments, both of the jaw members 410 and 420 may include a resilient conductive sealing surface. The sealing surface 412 may be formed as a conductive plate electrode having a proximal end 414 and a distal end 416. The sealing surface 412 is coupled at its proximal end 414 to a proximal end 415 of the jaw housing 411 and at its distal end 416 to a distal end 413 of the jaw housing 411. The sealing surface 412 may be supported within the jaw housing 411 of the jaw member 410 by a support member 418, which is not coupled thereto and prevents the sealing surface 412 from flexing inwardly. The sealing surfaces 412 and 422 may be formed from the same reversibly resilient materials as the sealing surfaces 212 and 122 of FIG. 3A and 3B.

The sealing surface 412 is precurved (e.g., concave) thereby putting the sealing surface 412 under a predetermined amount of strain. In embodiments, the sealing surface 422 may also be curved either in concave or convex manner with respect to the tissue T. In a convex configuration, curvature of the sealing surface 422 may be of substantially similar shape as the sealing surface 412 to allow for the tissue "T" to be evenly spread as the jaw members 410 and 420 are approximated thereabout. A concave configuration would allow the sealing surface 422 to distribute pressure exerted on the tissue similarly to the sealing surface 412.

During operation, the jaw members 410 and 420 are brought into the approximated position to proximate tissue T disposed between sealing surfaces 412 and 422 of jaw members 410, 420, respectively. Preloading of the sealing surface 412 allows for gradual increase in the pressure exerted on the tissue T as the pressure exerted by the jaw members 410 and 420 is partially absorbed by the sealing surface 412. In further embodiments, the sealing surface 412 may be formed as a leaf spring.

In one embodiment, the sealing surface 412 is configured to apply a predetermined amount of pressure to the tissue T from about 3 kilograms per centimeter ($kg/cm^2$) to about 16 $kg/cm^2$, in embodiments, from about 7 $kg/cm^2$ to about 12 $kg/cm^2$. This may be controlled by adjusting one or more of the following parameters including, but not limited to, dimensions of the sealing surface 412, material (e.g., tensile) properties of the sealing surface 412, and combinations thereof. The sealing surface 412 may include a width of from about 0.25 millimeters (mm) to about 25 mm, a length of from about 1 mm to about 100 mm, and a thickness of from about 0.002 mm to about 2.5 mm. The sealing surface 412 may have an elasticity expressed as a tensile or Young's modulus from about 69 GPa (gigapascals) to about 300 GPa.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    an end effector assembly including first and second jaw members moveable relative to one another between a first, spaced-apart position and a second, approximated position, wherein in the second position, the jaw members cooperate to define a cavity that is configured to receive tissue between the jaw members;
    an actuation member movably disposable within one of the first or second jaw members; and
    a resilient, electrically conductive sealing surface operably coupled to at least one of the first and second jaw members, the resilient, electrically conductive sealing surface having a movable proximal end, wherein the actuation member is configured to contact the movable proximal end of the resilient, electrically conductive sealing surface to cause the resilient, electrically conductive sealing surface to flex toward either one of the first jaw member or the second jaw member.

2. The surgical instrument according to claim 1, wherein each of the first and second jaw members includes a jaw housing.

3. The surgical instrument according to claim 2, wherein the resilient, electrically conductive sealing surface is disposed within the jaw housing of at least one of the first and second jaw members and includes a distal end coupled to the respective jaw housing.

4. The surgical instrument according to claim 3, wherein the jaw housing including the resilient, electrically conductive sealing surface includes a support member supporting the resilient, electrically conductive sealing surface and configured to force the resilient, electrically conductive sealing surface to flex away from the support member and against tissue when under compression.

5. The surgical instrument according to claim 3, wherein a longitudinal travel distance of the actuation member is proportional to the pressure applied to tissue by the resilient, electrically conductive sealing surface.

6. The surgical instrument according to claim 3, wherein the resilient, electrically conductive sealing surface is configured to engage tissue when compressive pressure is applied thereto to apply a pressure on tissue from about $3 kg/cm^2$ to about $16 kg/cm^2$.

7. The surgical instrument according to claim 1, wherein the actuation member is configured to move distally along a longitudinal axis defined by one of the first and second jaw members to distally move the movable proximal end of the resilient, electrically conductive sealing surface.

8. A surgical instrument, comprising:
    an end effector assembly including:
        first and second jaw members moveable relative to one another between a first, spaced-apart position and a second, approximated position, wherein, in the second position, the jaw members cooperate to define a cavity that is configured to receive tissue between the jaw members;
        a resilient, electrically conductive sealing surface operably coupled to at least one of the jaw members that is selectively flexible toward tissue grasped between the jaw members to apply a pressure to the tissue from about $3 kg/cm^2$ to about $16 kg/cm^2$, the resilient, electrically conductive sealing surface having a movable proximal end; and
        an actuation member movably disposable within one of the first or second jaw members and configured to contact the movable proximal end of the resilient, electrically conductive sealing surface to cause the resilient, electrically conductive sealing surface to flex toward either one of the first jaw member or the second jaw member.

9. The surgical instrument according to claim 8, wherein each of the first and second jaw members includes a jaw housing.

10. The surgical instrument according to claim 9, wherein the resilient, electrically conductive sealing surface is disposed within the jaw housing of at least one of the first and second jaw members and includes a distal end coupled to the respective jaw housing.

11. The surgical instrument according to claim 10, wherein the jaw housing including the resilient, electrically conductive sealing surface includes a support member supporting the resilient, electrically conductive sealing surface and configured to force the resilient, electrically conductive sealing surface to flex away from the support member and against tissue when under compression.

12. The surgical instrument according to claim 10, wherein a longitudinal travel distance of the actuation member is proportional to the pressure applied to tissue by the resilient, electrically conductive sealing surface.

13. The surgical instrument according to claim 10, wherein the resilient, electrically conductive sealing surface is configured to engage tissue when compressive pressure is applied thereto to apply a pressure on tissue from about $3 kg/cm^2$ to about $16 kg/cm^2$.

14. A method for sealing tissue comprising:
grasping tissue between first and second jaw members, the jaw members cooperating to define a cavity that is configured to receive the tissue; and
moving an actuation member to engage a movable proximal end of a resilient, electrically conductive sealing surface coupled to at least one of the first or second jaw members thereby causing the resilient, electrically conductive sealing surface to flex toward the grasped tissue.

15. The method according to claim 14, wherein each of the first and second jaw includes a jaw housing.

16. The method according to claim 14, wherein the jaw housing of least one of the first and second jaw members includes a support member supporting the resilient, electrically conductive sealing surface and configured to force the resilient, electrically conductive sealing surface to flex outwardly away from the support member and against tissue when under compression.

17. The method according to claim 14, wherein a longitudinal travel distance of the actuation member is proportional to the pressure applied to tissue by the resilient, electrically conductive sealing surface.

18. The method according to claim 14, wherein the resilient, electrically conductive sealing surface is configured to engage tissue when compressive pressure is applied thereto to apply a pressure on tissue from about 3 $kg/cm^2$ to about 16 $kg/cm^2$.

* * * * *